(12) United States Patent
Nielsen et al.

(10) Patent No.: US 8,623,332 B2
(45) Date of Patent: Jan. 7, 2014

(54) CHEWING GUM HAVING SUSTAINED RELEASE OF NICOTINE

(75) Inventors: Bruno Provstgaard Nielsen, Vejle Ost (DK); Jesper Neergaard, Aabenraa (DK)

(73) Assignee: Fertin Pharma A/S, Vejle (DK)

( * ) Notice: Subject to any disclaimer, the term of this patent is extended or adjusted under 35 U.S.C. 154(b) by 0 days.

(21) Appl. No.: 13/360,102

(22) Filed: Jan. 27, 2012

(65) Prior Publication Data

US 2013/0011343 A1 Jan. 10, 2013

(30) Foreign Application Priority Data

Jul. 6, 2011 (DK) .................................. 2011 00516

(51) Int. Cl.
*A61K 9/68* (2006.01)
(52) U.S. Cl.
USPC ............................................................. 424/48
(58) Field of Classification Search
USPC ............................................................. 424/48
See application file for complete search history.

(56) References Cited

U.S. PATENT DOCUMENTS

| | | | |
|---|---|---|---|
| 5,488,962 A | 2/1996 | Perfetti | |
| 2009/0196834 A1 | 8/2009 | Andersen | |
| 2010/0104688 A1 * | 4/2010 | Andersen et al. | 426/5 |
| 2010/0104689 A1 | 4/2010 | Thorengaard | |
| 2010/0255064 A1 | 10/2010 | Andersen et al. | |
| 2011/0064783 A1 | 3/2011 | Bang-Madsen et al. | |

FOREIGN PATENT DOCUMENTS

| | | |
|---|---|---|
| WO | 9613173 A1 | 5/1996 |
| WO | 0013662 A2 | 3/2000 |
| WO | 02071860 A1 | 9/2002 |
| WO | 2006000232 A1 | 1/2006 |
| WO | 2009143841 A1 | 12/2009 |

OTHER PUBLICATIONS

DKPTO: Search Report for Danish Patent Application No. PA 2011 00516 (counterpart application); Dec. 7, 2011; 2 pages.
European Pharmacopoeia, Council of Europe, Strasbourg Cedex, France; Fourth Edition; ISBN: 9287145873; Nov. 15, 2001; 4 pages.
European Pharmacopoeia, Council of Europe, Strasbourg Cedex, France; Sixth Edition; ISBN: 9287160546; Jul. 23, 2007; 3 pages.

* cited by examiner

*Primary Examiner* — Benjamin Packard
(74) *Attorney, Agent, or Firm* — Howison & Arnott, L.L.P.

(57) ABSTRACT

The present invention relates to a chewing gum having a high Surface Area to Volume ratio (SAV ratio), wherein said chewing gum comprises a water insoluble gum base matrix, a water soluble bulk portion and nicotine, wherein the gum base matrix, nicotine and the bulk portion are mixed and extruded to form a final extruded chewing gum product having a SAV ratio above 0.7, and wherein sustained release of nicotine is facilitated by adding 0.1-10% of C8-C10 triglycerides by weight of the chewing gum.

12 Claims, No Drawings

CHEWING GUM HAVING SUSTAINED RELEASE OF NICOTINE

CROSS-REFERENCE TO RELATED APPLICATIONS

This application claims benefit of Danish Patent Application Serial No. PA 2011 00516, filed Jul. 6, 2011, the specification of which is incorporated herein by reference in its entirety.

TECHNICAL FIELD

The present invention relates to the field of chewing gum. In particular the present invention relates to a chewing gum having sustained release of nicotine.

BACKGROUND

It is well known to use chewing gum comprising nicotine or complexes of nicotine to provide a user with appropriate doses of nicotine.

Considerable effort has been put into formulating chewing gum that can deliver nicotine to a user in a way close to what is experienced by a person when smoking a cigarette.

Different ways of incorporating the nicotine into the chewing gum by mixing or initial preparation of the nicotine have been disclosed in the prior art.

One of these prior art disclosures includes U.S. Pat. No. 5,488,962 specifically dealing with the problem of simulating the cigarette smoking with respect to the level of nicotine retention in the blood and saliva. According to the disclosure, an initial peak of nicotine level in the blood is obtained more similar to the corresponding absorption of nicotine when smoking a cigarette. The levels reached after a certain time corresponds to conventional nicotine-containing chewing gums.

A problem is, however, that a too high initial release may result in too much nicotine released, which may therefore cause a sense of burning in the mouth of a user.

It is therefore an object of the present invention to obtain a nicotine chewing gum with a sustained release of nicotine as compared to prior art nicotine-containing chewing gums.

SUMMARY

The present invention relates to a chewing gum, wherein said chewing gum comprises a water insoluble gum base matrix, a water soluble bulk portion and nicotine, wherein the gum base matrix, nicotine and the bulk portion are mixed and extruded to form a final extruded chewing gum product, and wherein sustained release of nicotine is facilitated by adding 0.1-10% of C8-C10 triglycerides by weight of the chewing gum.

According to some aspects of the present invention the addition of C8-C10 triglycerides to a chewing gum has surprisingly been found to affect the release of nicotine in chewing gum, preferably with comparatively high Surface Area to Volume ratio (SAV ratio), in a way that makes such chewing gum suitable for delivering nicotine in appropriate amounts to a person chewing a chewing gum according to the present invention.

It has been found by the present inventors that C8-C10 triglycerides in chewing gum, preferably with comparatively large surface areas, may both stabilize the nicotine in the chewing gum and facilitate a sustained release of the nicotine.

The phrase "sustained release" herein refers to a release of nicotine where the amount of nicotine released from the chewing gum over time, as the chewing gum is chewed, is somewhat delayed when compared to prior art nicotine chewing gum. Prior art chewing gum typically delivers an initial burst of nicotine and a relative high release of nicotine during the first few minutes of chewing. The sustained release of the inventive chewing gum implies that less nicotine is released during the first minutes of chewing where after the release gradually increases.

The initial burst of nicotine may be desirable in some cases but also has serious drawbacks, such as the effect of "burning" described below.

Because of these surprising effects of stabilization and sustainment of nicotine release further advantages are obtained according to embodiments of the invention.

Nicotine release from chewing gum with comparatively large surface areas is expected to be at least initially fast which may result in the unwanted effect of "burning", an unpleasant taste and sensation in the mouth. By adding efficient amounts of C8-C10 triglycerides to the chewing gum, this "burning" may be avoided. Thereby the quality and customer acceptance of such chewing gum may be greatly improved. The "burning" is primarily experienced during the first 5 minutes or so of chewing and this initial burning may be markedly less in the inventive chewing gum when compared to the prior art.

Furthermore it has also been established by the present inventors that a very favorable soft initial chew is obtained as a consequence of adding C8-C10 triglycerides to the chewing gum. Prior art nicotine chewing gum often may tend to possess a rather hard initial chew.

With respect to flavor, the taste intensity of the chewing gum according to the present invention compares well with the prior art. For other textural properties such as elasticity, the inventive chewing gum resembles prior art nicotine chewing gum very well.

In an embodiment of the invention, the C8-C10 triglycerides have a degree of saturation of at least 80%, such as at least 95%.

A very favorable texture of the chewing gum is obtained by using C8-C10 triglycerides having a high degree of saturation.

It has been found by the present inventors that an aspect relating to the present invention is the stability of the C8-C10 triglycerides with respect to e.g. oxidation.

According to an embodiment of the present invention, a relatively high degree of saturation of the C8-C10 triglycerides is preferable because the risk of oxidation and taste off-notes is diminished.

Furthermore, the possible amount of problematic trans-fatty-acids added to the chewing gum with the C8-C10 becomes insignificant when the C8-C10 triglycerides have a high degree of saturation.

In an embodiment of the invention, the SAV ratio of the chewing gum is above 0.7. In a further embodiment of the invention, the SAV ratio of the chewing gum is above 0.75, such as above 0.8.

Even though the chewing gum according to embodiments of the invention may have a comparatively large surface area and nicotine is vulnerable towards e.g. oxidation, it has surprisingly been found that the C8-C10 triglycerides added to the chewing gum stabilize the nicotine, whereby both an improved shelf life of the chewing gum is obtained and at the same time, an efficient use of the comparatively expensive nicotine is promoted.

In an embodiment of the invention, the SAV ratio of the chewing gum is below 3, such as below 1.

In an embodiment of the invention, the C8-C10 triglycerides comprise less than 1% unsaturated fatty acid triglycerides.

In an embodiment of the invention, the chewing gum comprises C8-C10 triglycerides in an amount of above 0.3%, such as above 0.5%, above 0.7%, above 0.9%, above 1.15%, or above 1.3% by weight of the chewing gum.

In an embodiment of the invention, the chewing gum comprises C8-C10 triglycerides in an amount of below 9%, such as below 8%, below 7%, below 6%, below 5%, or below 4% by weight of the chewing gum.

According to embodiments of the invention, depending on, among other factors, the SAV ratio of the chewing gum and the exact gum base composition, effective amounts of C8-C10 triglycerides to obtain some or all of the abovementioned effects and advantages are added to the chewing gum.

In an embodiment of the invention, the chewing gum comprises C2-C6 triglycerides in an amount of less than 1% by weight of the chewing gum, such as less than 0.5% or less than 0.3%.

A chewing gum with too large amounts of triglycerides of C6 or lower may have a too soft texture to give a pleasant chew feel. Furthermore, the release of nicotine will be faster than typically desired.

In an embodiment of the invention, the chewing gum comprises less than 1% by weight of the chewing gum of C12 or higher triglycerides added to the chewing gum together with the bulk portion, that is, as separate components outside the gum base, such as less than 0.5% or less than 0.3%.

A chewing gum with too large amounts of triglycerides of C12 or higher added as separate components outside the gum base may have a too hard texture to give a pleasant chew feel.

In an embodiment of the invention, the chewing gum formulation has a weight in the range of 0.1 to 10 grams, preferably in the range of 0.5 to 4 grams.

In an embodiment of the invention, the chewing gum has at least one dimension of less than 4 mm, such as less than 3 or 2 mm.

In an embodiment of the invention, the chewing gum comprises glycerin in an amount of between 0.001 and 2% by weight of the chewing gum, such as between 0.1 and 1.5% by weight.

In an embodiment of the invention, larger amounts of glycerin in the chewing gum tend to soften the chewing gum too much when combined with effective amounts of C8-C10 triglycerides. Furthermore, destabilization of nicotine may occur, if glycerin is present in the chewing gum in large amounts.

In some embodiments of the invention, comparatively small amounts of glycerin are highly desirable and an excellent texture of the chewing gum is obtained.

In an embodiment of the invention, the chewing gum comprises flavor and wherein the release of the flavor from the chewing gum is less affected by the addition of C8-C10 triglycerides than the release of nicotine from the chewing gum.

It has surprisingly been found by the present inventors that in an embodiment of the invention, the release of flavor from the chewing gum is less affected by the addition of C8-C10 triglycerides than the release of nicotine from the chewing gum. In this way, a very effective taste-masking of the nicotine is established, providing a chewing gum with an at least initially very pleasant taste, making such embodiment advantageous when compared to prior art products.

In an embodiment of the invention, said triglycerides impart a soft chew of the chewing gum.

Tests have shown that the novel chewing gum formulations comprising C8-C10 triglycerides may have a soft chew feel both initially and throughout the chew process which often is preferred over the rather hard chew feel of some prior art products. Although this is a more qualitative feature of some embodiments of the invention, the term "soft chew" is meaningful to those skilled in the art.

In an embodiment of the invention, the C8-C10 triglycerides are added as part of the chewing gum without being pre-mixed with chewing gum ingredients before the addition to the chewing gum.

By keeping the C8-C10 triglycerides separate from other chewing gum ingredients in the manufacturing process, an advantageous embodiment of the present invention has been obtained.

In an embodiment of the invention, the C8-C10 triglycerides are not added as part of an encapsulation system.

In an embodiment of the invention, the C8-C10 triglycerides are not added as part of the insoluble gum base matrix.

In an embodiment of the invention, the nicotine is added in the form of nicotine polacrilex.

In an embodiment of the invention, the chewing gum comprises nicotine in an amount of 0.5-8 mg, preferably 1-5 mg, such as 2 mg or 4 mg.

The amount of nicotine in chewing gum according to embodiments of the invention may be varied depending on the actual release profile and the purpose of a particular chewing gum product. Because of the sustained release from the inventive chewing gum, comparatively high loads of nicotine may be possible without negatively affecting the taste of the chewing gum. Also, due to the efficient and sustained administration of the nicotine to the person chewing the gum, low loads of nicotine are possible, while still providing nicotine in doses relieving such person from nicotine cravings.

In an embodiment of the invention, less than 1 mg nicotine, such as less than 0.7 mg or less than 0.5 mg, is released from the chewing gum within the first 5 minutes from initiation of a chewing process carried out in vitro on a chewing machine in accordance with European Pharmacopeia 4th. ed. 2.9.25, with a phosphate buffer with a pH of 7.4.

By adjusting the amounts of C8-C10 triglycerides in the chewing gum, the release of nicotine from the chewing gum may be influenced. Typically, the initial nicotine release from the chewing gum, when chewed, may be lower than the nicotine release would be without any C8-C10 glycerides added.

In an embodiment of the invention, less than 1.5 mg nicotine, such as less than 1.1 mg or less than 0.6 mg, is released from the chewing gum within the first 10 minutes from initiation of a chewing process carried out in vitro on a chewing machine in accordance with European Pharmacopeia 4th. ed. 2.9.25, with a phosphate buffer with a pH of 7.4.

According to embodiments of the invention, a relatively slow and sustained release is obtained through the addition of C8-C10 triglycerides to the chewing gum.

In an embodiment of the invention, less than 40% of the total nicotine content in the chewing gum, such as less than 28%, less than 20%, less than 15% or less than 10%, is released from the chewing gum within the first 5 minutes from initiation of a chewing process carried out in vitro on a chewing machine in accordance with European Pharmacopeia 4th. ed. 2.9.25, with a phosphate buffer with a pH of 7.4.

In an embodiment of the invention, less than 50% of the total nicotine content in the chewing gum, such as less than 38%, less than 28%, less than 20% or less than 15%, is released from the chewing gum within the first 10 minutes from initiation of a chewing process carried out in vitro on a chewing machine in accordance with European Pharmacopeia 4th. ed. 2.9.25, with a phosphate buffer with a pH of 7.4.

A nicotine chewing gum may typically be chewed for an extended period of time, e.g. 30 minutes. It may therefore be advantageous to apply chewing gum with a sustained release of nicotine providing efficient doses of nicotine throughout the chewing time. Different release profiles of nicotine may be obtained from chewing gum according to embodiments of the invention.

In one preferred embodiment, the nicotine release of the chewing gum when chewed, is slow initially (the first about 5 minutes), increases between about 5 and about 20 minutes and again slowing down after about 20 minutes of chewing. It has been found by the present inventors that this particular type of sustained release has some distinct advantages, including the diminishing of the earlier described "burning" and a very effective nicotine dosage during the period in time with increased release.

Another nicotine release profile that may be achieved with the application of C8-C10 triglycerides in a chewing gum according to another preferred embodiment of the invention and being quite different from typical prior art nicotine release profiles is a slow initial release (the first about 5 minutes), an increase between about 5 and about 20 minutes and a further increase after about 20 minutes of chewing.

An advantage of this type of sustained release may be that the user has an incitement to continue chewing the gum, because the relief from nicotine cravings becomes more efficient, the longer the chewing gum is chewed, due to the sustained and increasing release of nicotine. In this way it may be possible to reduce the frequency of taking a new chewing gum, whereby the overall nicotine uptake of the person using this particular embodiment of the present invention may be reduced.

In an embodiment of the invention, less than 65% of the total nicotine content in the chewing gum, such as less than 50%, less than 40% or less than 30%, is released from the chewing gum within the first 15 minutes from initiation of a chewing process carried out in vitro on a chewing machine in accordance with European Pharmacopeia 4th. ed. 2.9.25, with a phosphate buffer with a pH of 7.4.

In an embodiment of the invention, less than 25% of the total nicotine content in the chewing gum is released from the chewing gum within the first 15 minutes from initiation of a chewing process carried out in vitro on a chewing machine in accordance with European Pharmacopeia 4th. ed. 2.9.25, with a phosphate buffer with a pH of 7.4.

In an embodiment of the invention, the gum base comprises
elastomer in the range of 5-40% by weight of the gum base,
natural resin in the range of 8-45% by weight of the gum base, and
synthetic resin in the range of 5-50% by weight of the gum base.

The gum base composition may vary according to embodiments of the invention.

In an embodiment of the invention, the chewing gum comprises gum base in an amount of 15 to 95% by weight of the chewing gum, preferably 20 to 90% by weight, such as 30 to 80% by weight, 35 to 70% by weight or 40 to 60% by weight.

The gum base content of the chewing gum may vary according to embodiments of the invention.

In an embodiment of the invention, the chewing gum comprises gum base in an amount of 100 mg to 5000 mg, preferably 200 mg to 3000 mg, more preferably 300 mg to 2000 mg, such as 400 mg to 1500 mg or 600 mg to 1200 mg.

In an embodiment of the invention, the chewing gum comprises natural resins in an amount of 0.1 to 40%, preferably 1 to 30%, such as 3 to 25% or 5 to 20%, by weight of the chewing gum.

In an embodiment of the invention, the chewing gum comprises synthetic resins in an amount of 0.1 to 40%, preferably 1 to 30%, such as 3 to 25% or 5 to 20%, by weight of the chewing gum.

In an embodiment of the invention, the chewing gum comprises terpene resins in an amount of 2 to 15% by weight of the chewing gum.

In some embodiments, the amount of terpene resins may influence the release of nicotine.

In an embodiment of the invention, the chewing gum comprises elastomer in an amount of at least 2% by weight of the chewing gum formulation, preferably at least 4% by weight of the chewing gum.

In an embodiment of the invention, the chewing gum comprises elastomer in an amount of less than 35% by weight of the chewing gum, preferably less than about 25% by weight of the chewing gum such as less than 20%, 15% or 10% by weight of the chewing gum.

In an embodiment of the invention, the gum base matrix comprises fats in an amount of less than 15% by weight of the chewing gum or less than 10% by weight of the chewing gum.

Moreover, the invention relates to a chewing gum comprising a water insoluble gum base matrix and a water soluble bulk portion and nicotine, wherein the gum base matrix, nicotine and the bulk portion are mixed and extruded to form a final extruded chewing gum product, and wherein stability of nicotine is facilitated by adding less than 1.0% hydrophilic softeners by weight of the chewing gum and wherein sustained release of nicotine is facilitated by adding 0.1-10% of C8-C10 triglycerides by weight of said chewing gum.

By keeping the amount of hydrophilic softeners relatively low, an efficient utilization of the added nicotine has been obtained and a chewing gum with more predictable nicotine dosage has been obtained Moreover, the invention relates to a chewing gum comprising a water insoluble gum base matrix and a water soluble bulk portion and nicotine, wherein the gum base matrix, nicotine and the bulk portion are mixed and extruded to form a final extruded chewing gum product, and wherein sustained release of nicotine is facilitated by adding 0.1-10% of C8-C10 triglycerides by weight of said chewing gum.

According to the present invention the addition of C8-C10 triglycerides to a chewing gum has surprisingly been found to affect the release of nicotine in chewing gum in a way that makes such chewing gum suitable for delivering nicotine in appropriate amounts to a person chewing a chewing gum according to the present invention.

It has been found by the present inventors that C8-C10 triglycerides may both stabilize the nicotine in the chewing gum and facilitate a sustained release of the nicotine.

Because of these surprising effects of stabilization and sustainment of nicotine release further advantages are obtained according to embodiments of the invention.

Nicotine release from chewing gum is expected to be at least initially fast which may result in the unwanted effect of "burning", an unpleasant taste and sensation in the mouth. By adding efficient amounts of C8-C10 triglycerides to the chewing gum, this "burning" may be avoided. Thereby the quality and customer acceptance of such chewing gum may be greatly improved. The "burning" is primarily experienced during the first 5 minutes or so of chewing and this initial burning may be markedly less in the inventive chewing gum when compared to the prior art.

Furthermore it has also been established by the present inventors that a very favorable soft initial chew may be obtained as a consequence of adding C8-C10 triglycerides to the chewing gum. Prior art Nicotine chewing gum often may tend to possess a rather hard initial chew.

With respect to flavor, the taste intensity of the chewing gum according to the present invention compares well with the prior art. For other textural properties such as elasticity, the inventive chewing gum resembles prior art nicotine chewing gum well.

DETAILED DESCRIPTION

By the terms "gum base" and "gum base matrix" is meant the mainly water-insoluble and hydrophobic gum base ingredients that are mixed together before the bulk portion of the chewing gum is added.

The term "bulk portion" intends to mean the mainly water-soluble and hydrophilic chewing gum ingredients that are mixed into the gum base matrix after it has been made.

The term "weight of the chewing gum" or similar wording meaning the same is defined in the present context as weight of the chewing gum, not including the weight of an outer coating, such as a hard coating, soft coating, and the like.

By the phrase "texture" is meant a qualitative measure of the visco-elastic properties of the chewing gum and of the overall mouth-feel experienced by the user during the chewing process. Thus the term "texture" encompasses measurable quantities such as hardness and elasticity as well as more subjective parameters related to the chew-feel experienced by a user.

The phrase "hydrophobic" is used to describe the ability of a substance to dissolve in or blend with apolar substances such as e.g. oils, waxes and hydrocarbon-based polymers.

The phrase hydrophilic is used to describe the ability of a substance to dissolve in or blend with polar substances, such as e.g. water.

The term Surface Area to Volume ratio (SAV ratio) as used herein is a dimensionless ratio defined as the total surface area (SA) of the chewing gum measured in $mm^2$ multiplied by 1 mm and divided by the volume (V) of the same chewing gum measured in $mm^3$.

The SAV ratio is used to describe the exposure of the object to the surroundings relative to the size of the object. Usually, nicotine-containing chewing gum has a comparatively low SAV ratio. An essential reason for this is that nicotine is vulnerable to oxidation reactions and therefore, in the prior art, it has been advantageous to have as much nicotine somewhat protected from the atmosphere inside the chewing gum as opposed to close to a surface. Because of the surprising stabilization of nicotine when C8-C10 triglycerides are added to the chewing gum, the preferred format of the inventive chewing gum may surprisingly be one with a comparatively high SAV ratio.

When in the present invention a chewing process is mentioned, such chewing process is carried out in vitro on a chewing machine in accordance with European Pharmacopeia 4th. ed. 2.9.25, with a phosphate buffer with a pH of 7.4.

In some embodiments of the invention, a buffer is added, the buffer being selected from the group consisting of tris buffers, amino acid buffers, carbonate, including monocarbonate, bicarbonate or sesquicarbonate, glycerinate, phosphate, glycerophosphate, acetate, glyconate or citrate of an alkali metal, such as potassium and sodium, e.g. trisodium and tripotassium citrate, or ammonium, and mixtures thereof.

When buffer is used, a preferred buffer is sodium bicarbonate. In some embodiments buffer is not part of the chewing gum. In some other embodiments, buffer is part of the chewing gum. In some embodiments of the invention, the amount of buffer is 0.5 to 10% by weight of the chewing gum.

In some embodiments of the invention the buffer is selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

The buffer may to some extent be microencapsulated or otherwise coated as granules with polymers and/or lipids being less soluble in saliva than is the one or more buffering agents. Such microencapsulation controls the dissolution rate whereby is extended the time frame of the buffering effect.

However, in a presently preferred embodiment an alkaline buffer is preferred, such as sodium carbonate.

According to the invention a preferred amount of gum base matrix in the final chewing gum is above 30 percent by weight of the chewing gum core, such as above 35 percent by weight of the chewing gum core, such as above 40 percent by weight of the chewing gum core, such as above 45 percent by weight of the chewing gum core, such as about 40 percent by weight of the chewing gum core, such as about 47 percent by weight of the chewing gum core.

The formulation of gum bases can vary substantially depending on the particular product to be prepared and on the desired masticatory and other sensory characteristics of the final product. However, typical ranges (% by weight) of the gum base components are: 5 to 80% by weight elastomeric compounds, 5 to 80% by weight natural and/or synthetic resins (elastomer plasticizers), 0 to 40% by weight waxes, 5 to 35% by weight softener other than waxes, 0 to 50% by weight filler, and 0 to 5% by weight of miscellaneous ingredients such as antioxidants, colourants, etc. The gum base may comprise about 5 to about 95 percent, by weight, of the chewing gum, more commonly the gum base comprises 10 to about 60 percent, by weight, of the gum.

Elastomers provide the rubbery, cohesive nature to the gum, which varies depending on this ingredient's chemical structure and how it may be compounded with other ingredients. Elastomers suitable for use in the gum base and gum of the present invention may include natural or synthetic types.

Elastomer plasticizers vary the firmness of the gum base. Their specificity on elastomer inter-molecular chain interaction (plasticizing) along with their varying softening points cause varying degrees of finished gum firmness and compatibility when used in base. This may be important when one wants to provide more elastomeric chain exposure to the alkane chains of the waxes.

The elastomers (rubbers) employed in the gum base may vary depending upon various factors such as the type of gum base desired, the texture of gum formulation desired and the other components used in the formulation to make the final chewing gum product. The elastomer may be any water-insoluble polymer known in the art, and includes those gum polymers utilized for chewing gums and bubble gums. Illustrative examples of suitable polymers in gum bases include both natural and synthetic elastomers. For example, those polymers which are suitable in gum bases include, without limitation, natural substances (of vegetable origin) such as chicle gum, natural rubber, crown gum, nispero, rosidinha, jelutong, perillo, niger gutta, tunu, balata, guttapercha, lechi capsi, sorva, gutta kay, and the like, and mixtures thereof. Examples of synthetic elastomers include, without limitation, styrene-butadiene copolymers (SBR), polyisobutylene, isobutylene-isoprene copolymers, polyethylene, polyvinyl acetate and the like, and mixtures thereof.

Natural resins may be used according to the invention and may be natural rosin esters, often referred to as ester gums including as examples glycerol esters of partially hydrogenated rosins, glycerol esters of polymerised rosins, glycerol esters of partially dimerized rosins, glycerol esters of tally oil rosins, pentaerythritol esters of partially hydrogenated rosins, methyl esters of rosins, partially hydrogenated methyl esters of rosins, pentaerythritol esters of rosins, synthetic resins such as terpene resins derived from alpha-pinene, beta-pinene, and/or d-limonene, and natural terpene resins.

In an embodiment of the invention, the resin comprises terpene resins, e.g. derived from alpha-pinene, beta-pinene, and/or d-limonene, natural terpene resins, glycerol esters of gum rosins, tall oil rosins, wood rosins or other derivatives thereof such as glycerol esters of partially hydrogenated rosins, glycerol esters of polymerized rosins, glycerol esters of partially dimerized rosins, pentaerythritol esters of partially hydrogenated rosins, methyl esters of rosins, partially hydrogenated methyl esters of rosins or pentaerythritol esters of rosins and combinations thereof.

In an embodiment of the invention, said chewing gum ingredients are selected from the group consisting of bulk sweeteners, flavors, dry-binders, tabletting aids, anti-caking agents, emulsifiers, antioxidants, enhancers, absorption enhancers, buffers, high intensity sweeteners, softeners, colors, or any combination thereof.

In an embodiment of the invention, said emulsifiers are selected from the group of cyclodextrins, polyoxyethylene castor oil derivatives, polyoxyethylene alkyl ethers, macrogol alkyl ethers, block copolymers of ethylene and propylene oxides, polyoxyethylene alkyl ethers, polyoxyethylene glycols, polyoxyethylene sorbitan fatty acid esters, polyoxyethylene (20) sorbitan monostearates, polyoxyethylene (20) sorbitan monooleates, polyoxyethylene stearates, sobitan esters, diacetyl tartaric ester of monoglycerides, lactylated monoglycerides, or any combination thereof.

In an embodiment of the invention, said chewing gum comprises emulsifiers in an amount in the range of 0.1% to 25% by weight of said chewing gum.

Petroleum waxes aid in the curing of the finished gum made from the gum base as well as improve shelf life and texture. Wax crystal size influences the release of flavor. Those waxes high in iso-alkanes have a smaller crystal size than those waxes high in normal-alkanes, especially those with normal-alkanes of carbon numbers less than 30. The smaller crystal size allows slower release of flavor since there is more hindrance of the flavor's escape from this wax versus a wax having larger crystal sizes. The compatibility of gum bases made using normal-alkanic waxes is less when compared to gum bases made with iso-alkanic waxes.

Petroleum wax (refined paraffin and microcrystalline wax) and paraffin wax are composed of mainly straight-chained normal-alkanes and branched iso-alkanes. The ratio of normal-alkanes to iso-alkanes varies.

The normal-alkanic waxes typically have carbon chain lengths>C-18 but the lengths are not predominantly longer than C-30. The branched and ring structures are located near the end of the chain for those waxes that are predominantly normal-alkanic. The viscosity of normal-alkanic waxes is <10 mm2/s (at 100° C.) and the combined number average molecular weight is <600 g/mole.

The iso-alkanic waxes typically have carbon lengths that are predominantly greater than C-30. The branched chains and ring structures are located randomly along the carbon chain in those waxes that are predominantly iso-alkanic. The viscosity of iso-alkanic waxes is greater than 10 mm2/s (at 100° C.) and the combined number average molecular weight is >600 g/mole. Synthetic waxes are produced by means that are atypical for petroleum wax production and are thus not considered petroleum wax. The synthetic waxes may include waxes containing branched alkanes and copolymerized with monomers such as, but not limited to propylene, polyethylene, and Fischer Tropsch type waxes. Polyethylene wax is a synthetic wax containing alkane units of varying lengths having attached thereto ethylene monomers.

Waxes and fats are conventionally used for the adjustment of the texture and for softening of the chewing gum base when preparing chewing gum bases. In connection with the present invention, any conventionally used and suitable type of natural and synthetic wax and fat may be used, such as for instance rice bran wax, polyethylene wax, petroleum wax (refined paraffin and microcrystalline wax), sorbitan monostearate, tallow, propylene glycol, paraffin, beeswax, carnauba wax, candelilla wax, cocoa butter, degreased cocoa powder and any suitable oil or fat, as e.g. completely or partially hydrogenated vegetable oils or completely or partially hydrogenated animal fats.

Antioxidants prolong shelf life and storage of gum base, finished gum or their respective components including fats and flavor oils.

Antioxidants suitable for use in gum base include butylated hydroxyanisole (BHA), butylated hydroxytoluene (BHT), betacarotenes, tocopherols, acidulants such as Vitamin C, propyl gallate, other synthetic and natural types or mixtures thereof. In an embodiment of the invention, said nicotine is in a form selected from nicotine salts, nicotine free base, nicotine bound in a complex, or any combination thereof.

In an embodiment of the invention, said complex comprises an ion exchange resin.

In an embodiment of the invention, said ion exchange resin is a weakly acidic cation exchange resin.

According to an embodiment of the invention, a preferred example of a weakly acidic cation exchange resin is polacrilex.

In an embodiment of the invention, said complex comprises an adsorbent.

In an embodiment of the invention, said adsorbent is selected from the group consisting of finely divided silicic acid, amorphous silica, magnesium silicate, calcium silicate, kaolin, clays, crystalline aluminosilicates, macaloid bentonite, activated carbon, alumina, hydroxylapatite, microcrystalline cellulose, or any combination thereof.

In an embodiment of the invention, said nicotine salts are selected from the group comprising nicotine hydrochloride, nicotine dihydrochloride, nicotine monotartrate, nicotine bitartrate, nicotine sulfate, nicotine zinc chloride, nicotine salicylate, or any combination thereof.

In an embodiment of the invention, the chewing gum comprises sweeteners, such as bulk sweeteners, sugar sweeteners, sugar substitute sweeteners, artificial sweeteners, high-intensity sweeteners, or any combination thereof.

Suitable bulk sweeteners include both sugar and non-sugar sweetening components. Bulk sweeteners typically constitute from about 5 to about 95% by weight of the chewing gum, more typically about 20 to about 80% by weight such as 30 to 70% or 30 to 60% by weight of the gum.

Useful sugar sweeteners are saccharide-containing components commonly known in the chewing gum art including, but not limited to, sucrose, dextrose, maltose, dextrins, trehalose, D-tagatose, dried invert sugar, fructose, levulose, galactose, corn syrup solids, and the like, alone or in combination.

Sorbitol can be used as a non-sugar sweetener. Other useful non-sugar sweeteners include, but are not limited to, other sugar alcohols such as mannitol, xylitol, hydrogenated starch hydrolysates, maltitol, isomalt, erythritol, lactitol and the like, alone or in combination.

High intensity artificial sweetening agents can also be used alone or in combination with the above sweeteners. Preferred high intensity sweeteners include, but are not limited to sucralose, aspartame, salts of acesulfame, alitame, saccharin and its salts, cyclamic acid and its salts, glycyrrhizin, dihydrochalcones, thaumatin, monellin, sterioside and the like, alone or in combination. In order to provide longer lasting sweetness and flavor perception, it may be desirable to encapsulate or otherwise control the release of at least a portion of the artificial sweeteners. Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another chewing gum component such as a resinous compound.

Usage level of the artificial sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (preferably from about 0.02 to about 8% by weight). When carriers used for encapsulation are included, the usage level of the encapsulated sweetener will be proportionately higher. Combinations of sugar and/or non-sugar sweeteners may be used in the chewing gum.

A chewing gum and/or gum base may, if desired, include one or more fillers/texturisers including as examples, magnesium and calcium carbonate, sodium sulphate, ground limestone, silicate compounds such as magnesium and aluminum silicate, kaolin and clay, aluminum oxide, silicium oxide, talc, titanium oxide, mono-, di- and tri-calcium phosphates, cellulose polymers, such as wood, and combinations thereof.

A number of chewing gum components well known within the art may be applied within the scope of the present invention. Such components comprise but are not limited to waxes, fats, softeners, fillers, flavors, anti-oxidants, emulsifiers, colouring agents, binding agents and acidulants According to embodiments of the invention, the C8 triglycerides comprise triglycerides of caprylic acid and/or the C10 triglycerides comprise triglycerides of capric acid. According to embodiments of the invention, the chewing gum is a stick chewing gum.

In an embodiment of the invention, the chewing gum is provided with an outer coating selected from the group consisting of hard coating, soft coating and edible film-coating or any combination thereof.

The following non-limiting examples illustrate different variations of the present invention. The examples are meant for indicating the inventive concept; hence the mentioned examples should not be understood as exhaustive for the present invention.

EXAMPLES

Example 1

Preparation of Gum Base

A gum base is prepared, which comprises the following ingredients.

| Ingredients | % by weight |
|---|---|
| Elastomer | 10 |
| Natural resin | 28 |
| Synthetic resin | 22 |
| Fat/wax/emulsifiers | 23 |
| Fillers | 17 |

It should be emphasized that several other gum base compositions may be applied within the scope of the invention.

The elastomer and filler are added to a mixing kettle provided with mixing means like e.g. horizontally placed Z-shaped arms. The kettle has been preheated for 15 minutes to a temperature of about 120° C. The rubber is sheared and grinded with mechanical action in the kettle.

Resin is slowly added to the elastomer and filler until the mixture becomes homogeneous. The remaining resin is then added to the kettle and mixed for 10-20 minutes. The softening ingredients are added and mixed for 20-40 minutes until the whole mixture becomes homogeneous.

The mixture is then discharged into the pan and allowed to cool to room temperature from the discharged temperature of 120° C.

Example 2

Preparation of Nicotine-Containing Chewing Gum

Chewing gum is prepared by use of the gum base in example 1 and according to a conventional mechanical mixing procedure during moderate use of heating as described below.

|  | CG1 | CG2 | CG3 | CG4 | CG5 |
|---|---|---|---|---|---|
| Gum base | 43.4% | 43.4% | 43.4% | 43.4% | 43.4% |
| Filler | 14.6% | 14.6% | 14.6% | 14.6% | 14.6% |
| Nicotine Polacrilex |  |  |  |  |  |
| Nicotine | 0.2% | 0.2% | 0.2% | 0.2% | 0.2% |
| Ion exchange resin | 0.8% | 0.8% | 0.8% | 0.8% | 0.8% |
| Buffer agents |  |  |  |  |  |
| Sodium hydrogen carbonate | 1.0% | 1.0% | 1.0% | 1.0% | 1.0% |
| Sodium carbonate | 2.0% | 2.0% | 2.0% | 2.0% | 2.0% |
| C8 | 0.0% | 1.3% | 2.6% | 5.2% | 7.8% |
| C10 | 0.0% | 0.7% | 1.4% | 2.8% | 4.2% |
| Sorbitol powder | 34.6% | 31.4% | 30.6% | 26.6% | 22.6% |
| Glycerin | 0.0% | 1.2% | 0.0% | 0.0% | 0.0% |
| Intense sweetener | 0.4% | 0.4% | 0.4% | 0.4% | 0.4% |
| Flavor | 3.0% | 3.0% | 3.0% | 3.0% | 3.0% |

Gum base and filler are mixed batch-wise in a mixing kettle provided with mixing means like e.g. horizontally placed Z-shaped arms. The kettle has been preheated to a temperature of up to approximately 50° C.

When the content is homogenous the other ingredient is added according to a specified time schedule. Nicotine is added in the first half of the mixing process and can be added as pure nicotine, as a nicotine salt or bound to an ion exchange resin, e.g. Amberlite IRP 64.

Finally, after mixing, chewing gums are formed through extrusion and rolling into chewing gum sticks.

Alternatively, the mixing step may be performed continuously in a conventional extruder process, partly or fully replacing the mixing involving the Z-blade mixer.

The pieces may be formulated with 0.1-8 mg of nicotine per piece, preferably 2 or 4 mg. The pieces evaluated below comprise 2 mg nicotine.

Example 3

Evaluation of Nicotine Release of CG1-CG4

Samples were evaluated by a test panel of 10 persons. The perceptual release is evaluated with respect to taste of the released nicotine. Each person could give a value between 0 and 10 and the sums of these values are presented in table 1. The sensory analyses were in general carried out in line with ISO 4121-2003.

TABLE 1

Perceptual nicotine release, sums of 10 test persons values. The time given is from initiation of a chewing process.

| Amount of C8 and C10 | perceptual release | | | |
|---|---|---|---|---|
| % by weight | 5 min | 10 min | 20 min | 30 min |
| CG1 | 0 | 42 | 58 | 75 | 85 |
| CG2 | 2 | 12 | 20 | 41 | 80 |
| CG3 | 4 | 10 | 19 | 48 | 79 |
| CG4 | 8 | 6 | 11 | 37 | 74 |

The nicotine release was increasingly sustained as the amount of C8 and C10 increased. As such, the amount of C8 and C10 may be used to adjust the release profile of nicotine according to what is desired.

Example 4

Evaluation of Softness of CG1-CG5

A test panel of 10 persons was used. The softness is characterized through a sensory evaluation. The reference evaluation of softness is referred to as A=hard, B=medium, C=soft, D=too soft. The values given from the test persons were collected and united into one average evaluation, which are presented in table 2.

TABLE 2

Sensory evaluation of the softness of chewing gums CG1-CG5. The time given is from initiation of a chewing process.

| Amount of C8 and C10 | Evaluation of softness | | | |
|---|---|---|---|---|
| % by weight | 2 min | 4 min | 6 min | 8 min |
| CG1 | 0 | A | A | B | B |
| CG2 | 2 | B | B | C | C |
| CG3 | 4 | C | C | C | C |
| CG4 | 8 | C | C | C | D |
| CG5 | 12 | C | C | D | D |

The chewing gums turned softer as the amount of C8 and C10 increased. For a total amount of 12%, the chewing gum turned too soft over time. For a total amount of 8%, the chewing gum was very close to turning unpleasantly soft for chewing.

Example 5

Evaluation of Nicotine Release

The nicotine release was measured in vitro on two chewing gums CG6 and CG7 according to embodiments of the present invention with a total of 2% and 4%, respectively, of C8 and C10 as compared to a prior art chewing gum without any C8 and C10.

The measurements were carried out according to the procedure set forth in the Ph. Eur. $6^{th}$ ed. 2.9.25, at pH=7.4, a chewing rate of 60 chew per minute, and with the temperature of the medium at 37° C.

The nicotine content of the samples before and after chewing was analyzed according to standard HPLC-techniques.

TABLE 3

Nicotine release. The time given is from initiation of a chewing process as described.

| Amount of C8 and C10 | Nicotine release (% AC (Actual Content)) | | | |
|---|---|---|---|---|
| % by weight | 5 min | 10 min | 20 min | 30 min |
| Prior art CG | 0 | 58 | 75 | 87 | 92 |
| CG6 | 2 | 18 | 35 | 58 | 80 |
| CG7 | 4 | 4 | 8 | 32 | 76 |

Example 6

Evaluation of Nicotine Release Versus Flavor Release for CG7

The nicotine release and the flavor release of CG7 and Prior art CG were measured. All values are given as percent by weight of total amount of the ingredient in question. The flavor in this specific measurement was peppermint.

The measurements were carried out according to the procedure set forth in the Ph. Eur. $6^{th}$ ed. 2.9.25, at pH=7.4, a chewing rate of 60 chew per minute, and with the temperature of the medium at 37° C.

TABLE 4

Nicotine release compared to flavor release. The time given is from initiation of a chewing process as described.

| | Amount of C8 and C10 % by weight | 5 min | 10 min | 20 min | 30 min |
|---|---|---|---|---|---|
| | | Nicotine release (% AC (Actual Content)) | | | |
| Prior art CG | 0 | 58 | 75 | 87 | 92 |
| CG7 | 4 | 4 | 8 | 32 | 76 |
| | | Flavor release (% AC (Actual Content)) | | | |
| Prior art CG | 0 | 28 | 36 | 43 | 47 |
| CG7 | 4 | 20 | 28 | 34 | 39 |

For the prior art CG, it is seen that the release of nicotine and flavor is more or less synchronized. However, when a total amount of 4% of C8 and C10 is present in the chewing gum, CG7, the flavor release is only slightly sustained, whereas the nicotine release is highly sustained.

Although the release data given above also depend on e.g. the gum base composition, a general trend confirming the surprising differentiating effects of C8 and C10 triglycerides between release of flavor and nicotine has been observed.

Example 7

Evaluation of Softness when Using Various Triglycerides

Chewing gum samples were prepared according to embodiments of the present invention with 4% triglyceride added as a separate component. The triglycerides used were of varying fatty acid chain length (denoted by the number of C atoms in the fatty acid employed).

A test panel of 10 persons was used. The softness is characterized through a sensory evaluation. The values given from the test persons were collected and united into one average evaluation, which are presented in table 5.

TABLE 5

Sensory evaluation of the softness of chewing gums

| | Amount (% by weight) | | | | | Evaluation |
|---|---|---|---|---|---|---|
| | C2 | C6 | C8 | C10 | C12 | C14 | of softness over time |
| CG10 | 4 | 0 | 0 | 0 | 0 | 0 | Too soft, unpleasant to chew |
| CG11 | 0 | 4 | 0 | 0 | 0 | 0 | Too soft, unpleasant to chew |
| CG12 | 0 | 0 | 4 | 0 | 0 | 0 | Excellent softness |
| CG13 | 0 | 0 | 0 | 4 | 0 | 0 | Excellent softness |
| CG14 | 0 | 0 | 0 | 0 | 4 | 0 | Too hard, unpleasant to chew |
| CG15 | 0 | 0 | 0 | 0 | 0 | 4 | Too hard, unpleasant to chew |
| CG16 | 0 | 0.4 | 2.0 | 1.6 | 0 | 0 | Slightly soft but pleasant to chew |
| CG17 | 0 | 0 | 1.8 | 1.9 | 0.2 | 0.1 | Slightly hard but pleasant to chew |

It is clearly seen that C8 and C10 are the two highly preferable triglycerides. For triglycerides derived from shorter acids, the chewing gum turns too soft and for triglycerides derived from longer acids, the chewing gum turns too hard. However, it is seen that smaller amounts of smaller or larger triglycerides may be present while still maintaining acceptable texture.

Example 8

Evaluation of Burning from Nicotine Release

Samples were evaluated by a test panel of 10 persons. The burning sensation was given an intensity value from 0 (no burning) to 6 (high burning). The values given from the test persons were collected and united into one average evaluation, which are presented in table 6. The sensory analyses were in general carried out in line with ISO 4121-2003.

TABLE 6

Burning sensation, average of 10 test persons values. The time given is from initiation of a chewing process.

| Amount of C8 and | Burning sensation over time (seconds) | | | | | | |
|---|---|---|---|---|---|---|---|
| C10 % by weight | 15 | 70 | 130 | 250 | 310 | 490 | 550 |
| CG20 0 | 1.4 | 2.6 | 3.6 | 4.0 | 3.9 | 2.7 | 2.3 |
| CG21 Between 2 and 4 | 1.2 | 2.1 | 2.6 | 2.5 | 2.7 | 2.8 | 2.8 |

The nicotine release was increasingly sustained as the amount of C8 and C10 increased. As such, the amount of C8 and C10 may be used to adjust the release profile of nicotine according to what is desired.

Example 9

Further Measurements

Further measurements were carried out with further chewing gums with varying contents of nicotine, elastomers, resins and buffer. In general these showed advantageous properties related to using C8 and C10 triglycerides when desiring a sustained release of nicotine as compared to conventional chewing gum.

What is claimed is:

1. Chewing gum having a high Surface Area to Volume ratio (SAV ratio), wherein said chewing gum comprises:
   a water insoluble gum base matrix,
   a water soluble bulk portion and nicotine,
   wherein the gum base matrix, nicotine and the bulk portion are mixed and extruded to form a final extruded chewing gum product having a SAV ratio above 0.7, and wherein sustained release of nicotine is facilitated by adding 0.1-10% of C8-C10 triglycerides by weight of the chewing gum, whereby less than 50% of the total nicotine content in the chewing gum is released from the chewing gum within the first 10 minutes from initiation of a chewing process carried out in vitro on a chewing machine in accordance with European Pharmacopeia 4th. ed. 2.9.25, with a phosphate buffer with a pH of 7.4.

2. Chewing gum according to claim 1, wherein the C8-C10 triglycerides have a degree of saturation of at least 80%.

3. Chewing gum according to claim 1, wherein the chewing gum comprises glycerin in an amount of between 0.001 and 2% by weight of the chewing gum.

4. Chewing gum according to claim 1, wherein the chewing gum comprises flavor and wherein the release of the flavor from the chewing gum is less affected by the addition of C8-C10 triglycerides than the release of nicotine from the chewing gum.

5. Chewing gum according to claim 1, wherein the C8-C10 triglycerides are added as part of the chewing gum without being pre-mixed with chewing gum ingredients before the addition to the chewing gum.

6. Chewing gum according to claim 1, wherein the C8-C10 triglycerides are not added as part of an encapsulation system.

7. Chewing gum according to claim 1, wherein the C8-C10 triglycerides are not added as part of the insoluble gum base matrix.

8. Chewing gum according to claim 1, wherein the chewing gum comprises nicotine in an amount of 0.5-8 mg.

9. Chewing gum according to claim 1, wherein the gum base comprises:
   elastomer in the range of 5-40% by weight of the gum base;
   natural resin in the range of 8-45% by weight of the gum base; and synthetic resin in the range of 5-50% by weight of the gum base.

10. Chewing gum according to claim 1, wherein the nicotine is added in the form of nicotine polacrilex.

11. Chewing gum comprising a water insoluble gum base matrix and a water soluble bulk portion and nicotine, wherein the gum base matrix, nicotine and the bulk portion are mixed and extruded to form a final extruded chewing gum product, and wherein stability of nicotine is facilitated by adding less than 1.0% hydrophilic softeners by weight of the chewing gum and wherein sustained release of nicotine is facilitated by adding 0.1-10% of C8-C10 triglycerides by weight of said chewing gum whereby less than 50% of the total nicotine content in the chewing gum is released from the chewing gum within the first 10 minutes from initiation of a chewing process carried out in vitro on a chewing machine in accordance with European Pharmacopeia 4th. ed. 2.9.25, with a phosphate buffer with a pH of 7.4.

12. Chewing gum comprising a water insoluble gum base matrix and a water soluble bulk portion and nicotine, wherein the gum base matrix, nicotine and the bulk portion are mixed and extruded to form a final extruded chewing gum product, and wherein sustained release of nicotine is facilitated by adding 0.1-10% of C8-C10 triglycerides by weight of said chewing gum whereby the nicotine release profile of the chewing gum upon chewing includes an initial first rate for the first five minutes of chewing, a second increased rate between five and twenty minutes of chewing and a third rate, less than the second rate, after twenty minutes.

* * * * *